(12) United States Patent
Nielsen et al.

(10) Patent No.: US 8,994,382 B2
(45) Date of Patent: Mar. 31, 2015

(54) ABSOLUTE POSITION DETERMINATION OF MOVABLY MOUNTED MEMBER IN MEDICATION DELIVERY DEVICE

(75) Inventors: Preben Nielsen, Holbæk (DK); Bodo von Münchow, Lyngby (DE); Peter Grønning Sørensen, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 1398 days.

(21) Appl. No.: 12/295,430

(22) PCT Filed: Apr. 12, 2007

(86) PCT No.: PCT/EP2007/053558
§ 371 (c)(1),
(2), (4) Date: Nov. 5, 2009

(87) PCT Pub. No.: WO2007/116090
PCT Pub. Date: Oct. 18, 2007

(65) Prior Publication Data
US 2011/0181301 A1 Jul. 28, 2011

Related U.S. Application Data

(60) Provisional application No. 60/796,099, filed on Apr. 28, 2006.

(30) Foreign Application Priority Data

Apr. 12, 2006 (EP) .................................... 06007633

(51) Int. Cl.
*G01R 27/28* (2006.01)
*A61M 5/315* (2006.01)
*G01D 5/165* (2006.01)

(52) U.S. Cl.
CPC ....... *A61M 5/31525* (2013.01); *A61M 5/31533* (2013.01); *A61M 5/3155* (2013.01); *A61M 5/31556* (2013.01); *A61M 2205/3317* (2013.01); *G01D 5/1655* (2013.01)
USPC .......................................... 324/649; 324/660

(58) Field of Classification Search
CPC ..................... A61M 5/31525; A61M 5/31533; C01D 6/1666
USPC ........................................................ 324/649
See application file for complete search history.

(56) References Cited

U.S. PATENT DOCUMENTS 3,700,862 A    10/1972    Snook et al.
3,809,863 A    5/1974     Oberg
(Continued)

FOREIGN PATENT DOCUMENTS

CN    1013704    8/1991
CN    1051152    9/1993
(Continued)

OTHER PUBLICATIONS

International Search Report for PCT/EP2007/054069, dated Sep. 17, 2007.
(Continued)

*Primary Examiner* — Thomas F Valone
(74) *Attorney, Agent, or Firm* — Wesley A. Nicolas; Reza Green; Richard W. Bork

(57) ABSTRACT

The present invention relates to a medication delivery device for expelling set doses of medicament, the medication delivery device comprising a position determining arrangement for detecting absolute positions of a movably mounted member, such as a dose indicator barrel, relative to a housing of the medication delivery device. The position determining arrangement comprises a plurality of electrically conducting electrodes arranged on an outer surface of the movably mounted member, and a plurality of contacts members fixedly arranged relative to the housing of the medication delivery device. A first and a second contact member are arranged to follow a first path across the electrically conducting electrodes upon movement of the movably mounted member relative to the housing, whereas a third and a fourth contact member are arranged to follow a second path across the electrically conducting electrodes upon movement of the movably mounted member relative to the housing.

25 Claims, 5 Drawing Sheets

(56) References Cited

U.S. PATENT DOCUMENTS

| | | | |
|---|---|---|---|
| 3,916,157 A | 10/1975 | Roulette et al. | |
| 3,998,513 A | 12/1976 | Kobayashi et al. | |
| 4,179,212 A | 12/1979 | Lahr | |
| 4,327,283 A | 4/1982 | Heyman et al. | |
| 4,355,300 A | 10/1982 | Weber | |
| 4,420,754 A | 12/1983 | Andermo | |
| 4,449,042 A | 5/1984 | Hampson et al. | |
| 4,476,149 A | 10/1984 | Poppe et al. | |
| 4,476,381 A | 10/1984 | Rubin | |
| 4,543,526 A * | 9/1985 | Burckhardt et al. | 324/725 |
| 4,591,707 A | 5/1986 | Stenzel et al. | |
| 4,625,101 A | 11/1986 | Hinks et al. | |
| 4,636,786 A | 1/1987 | Haertling | |
| 4,693,574 A | 9/1987 | Ohnuki et al. | |
| 4,731,526 A | 3/1988 | Knoll et al. | |
| 4,739,377 A | 4/1988 | Allen | |
| 4,810,867 A | 3/1989 | Speicher | |
| 4,850,966 A | 7/1989 | Grau et al. | |
| 4,853,521 A | 8/1989 | Claeys et al. | |
| 4,857,716 A | 8/1989 | Gombrich et al. | |
| 4,880,014 A | 11/1989 | Zarowitz et al. | |
| 4,896,946 A | 1/1990 | Suzuki et al. | |
| 4,930,263 A | 6/1990 | Rando | |
| 4,950,246 A | 8/1990 | Muller | |
| 4,959,056 A | 9/1990 | Dombrowski et al. | |
| 4,978,335 A | 12/1990 | Arthur | |
| 5,053,715 A | 10/1991 | Andermo | |
| 5,059,776 A | 10/1991 | Antes | |
| 5,077,635 A | 12/1991 | Bollhagen et al. | |
| 5,078,683 A | 1/1992 | Sancoff et al. | |
| 5,091,798 A | 2/1992 | Hibino | |
| 5,132,026 A | 7/1992 | Baluyot et al. | |
| 5,153,827 A | 10/1992 | Courte et al. | |
| 5,174,766 A | 12/1992 | Yoshizawa et al. | |
| 5,176,502 A | 1/1993 | Sanderson et al. | |
| 5,196,683 A | 3/1993 | Marom et al. | |
| 5,271,527 A | 12/1993 | Haber et al. | |
| 5,305,147 A | 4/1994 | Hasegawa et al. | |
| 5,311,364 A | 5/1994 | Kanoshima et al. | |
| 5,317,506 A | 5/1994 | Coutre et al. | |
| 5,336,871 A | 8/1994 | Colgate | |
| 5,379,131 A | 1/1995 | Yamazaki | |
| 5,394,206 A | 2/1995 | Cocca | |
| 5,403,616 A | 4/1995 | Hattori et al. | |
| 5,418,649 A | 5/1995 | Igarashi | |
| 5,422,472 A | 6/1995 | Tavislan et al. | |
| 5,430,278 A | 7/1995 | Krieg et al. | |
| 5,432,329 A | 7/1995 | Colgate et al. | |
| 5,461,239 A | 10/1995 | Atherton | |
| 5,523,560 A | 6/1996 | Manique et al. | |
| 5,569,212 A | 10/1996 | Brown | |
| 5,585,615 A | 12/1996 | Iwanami et al. | |
| 5,593,390 A | 1/1997 | Castellano et al. | |
| 5,628,309 A | 5/1997 | Brown | |
| 5,637,854 A | 6/1997 | Thomas | |
| 5,643,212 A | 7/1997 | Coutre et al. | |
| 5,675,380 A | 10/1997 | Florent et al. | |
| 5,686,725 A | 11/1997 | Maruyama et al. | |
| 5,747,350 A | 5/1998 | Sattler | |
| 5,757,521 A | 5/1998 | Walters et al. | |
| 5,764,457 A | 6/1998 | Uhde et al. | |
| 5,777,303 A | 7/1998 | Berney | |
| 5,782,814 A | 7/1998 | Brown et al. | |
| 5,786,584 A | 7/1998 | Button et al. | |
| 5,791,880 A | 8/1998 | Wilson | |
| 5,792,117 A | 8/1998 | Brown | |
| 5,793,502 A | 8/1998 | Bianco et al. | |
| 5,821,521 A | 10/1998 | Bridgelall et al. | |
| 5,821,524 A | 10/1998 | Horlbeck et al. | |
| 5,876,380 A | 3/1999 | Manganini et al. | |
| 5,880,683 A | 3/1999 | Brandestini | |
| 5,882,463 A | 3/1999 | Tompkin et al. | |
| 5,886,519 A * | 3/1999 | Masreliez et al. | 324/207.17 |
| 5,895,369 A | 4/1999 | Flower | |
| 5,902,990 A | 5/1999 | Stewart | |
| 5,920,198 A | 7/1999 | Suzuki et al. | |
| 5,925,867 A | 7/1999 | Hagimoto | |
| 5,928,201 A * | 7/1999 | Poulsen et al. | 604/208 |
| 5,954,700 A | 9/1999 | Kovelman | |
| 5,986,585 A | 11/1999 | Pusch | |
| 6,003,775 A | 12/1999 | Ackley | |
| 6,019,745 A | 2/2000 | Gray | |
| 6,047,892 A | 4/2000 | Schuessler et al. | |
| 6,053,415 A | 4/2000 | Norwood | |
| 6,068,615 A | 5/2000 | Brown et al. | |
| 6,090,064 A | 7/2000 | Reilly et al. | |
| 6,110,148 A | 8/2000 | Brown et al. | |
| 6,110,152 A | 8/2000 | Kovelman | |
| 6,168,080 B1 | 1/2001 | Verschuur et al. | |
| 6,177,683 B1 | 1/2001 | Kolesar et al. | |
| 6,202,929 B1 | 3/2001 | Verschuur et al. | |
| 6,215,508 B1 | 4/2001 | Bryan et al. | |
| 6,265,466 B1 | 7/2001 | Glatkowski et al. | |
| 6,274,092 B1 | 8/2001 | Itoh | |
| 6,329,813 B1 | 12/2001 | Andermo | |
| 6,352,523 B1 | 3/2002 | Brown et al. | |
| 6,372,293 B1 | 4/2002 | Mathus et al. | |
| 6,435,175 B1 | 8/2002 | Stenzler | |
| 6,475,192 B1 | 11/2002 | Reilly et al. | |
| 6,533,183 B2 | 3/2003 | Aasmul et al. | |
| 6,598,796 B2 | 7/2003 | Harrop | |
| 6,652,812 B1 | 11/2003 | Vartiainen et al. | |
| 6,669,090 B2 | 12/2003 | Eilersen | |
| 6,700,391 B2 | 3/2004 | Strack et al. | |
| 6,813,868 B2 | 11/2004 | Baldwin et al. | |
| 6,854,653 B2 | 2/2005 | Eilersen | |
| 6,876,209 B2 | 4/2005 | Lin et al. | |
| 6,954,700 B2 | 10/2005 | Higashida et al. | |
| 6,957,522 B2 | 10/2005 | Baldwin et al. | |
| 6,976,349 B2 | 12/2005 | Baldwin et al. | |
| 6,994,261 B2 | 2/2006 | Eilersen | |
| 7,018,363 B2 | 3/2006 | Cowan et al. | |
| 7,041,941 B2 | 5/2006 | Faries et al. | |
| 7,061,831 B2 | 6/2006 | De La Huerga | |
| 7,077,332 B2 | 7/2006 | Verschuur et al. | |
| 7,104,973 B2 | 9/2006 | Woolston et al. | |
| 7,108,184 B2 | 9/2006 | Mase et al. | |
| 7,138,806 B2 | 11/2006 | Gafner et al. | |
| 7,426,408 B2 * | 9/2008 | DeNuzzio et al. | 600/345 |
| 7,521,921 B2 * | 4/2009 | Zhu et al. | 324/207.17 |
| 7,614,545 B2 * | 11/2009 | Christoffersen et al. | 235/375 |
| 7,621,456 B2 | 11/2009 | Eilersen | |
| 8,049,519 B2 | 11/2011 | Nielsen et al. | |
| 8,197,449 B2 * | 6/2012 | Nielsen et al. | 604/189 |
| 8,348,904 B2 * | 1/2013 | Petersen | 604/207 |
| 2001/0001472 A1 | 5/2001 | Sano et al. | |
| 2001/0013544 A1 | 8/2001 | Rathus et al. | |
| 2001/0015202 A1 | 8/2001 | Miller | |
| 2001/0034506 A1 | 10/2001 | Hirschman et al. | |
| 2002/0000471 A1 | 1/2002 | Aasmul et al. | |
| 2002/0012176 A1 | 1/2002 | Ning | |
| 2002/0020654 A1 | 2/2002 | Eilersen | |
| 2002/0022821 A1 | 2/2002 | Eilersen | |
| 2002/0063156 A1 | 5/2002 | Marchand | |
| 2002/0106309 A1 | 8/2002 | Mathus et al. | |
| 2002/0117549 A1 | 8/2002 | Lee | |
| 2002/0117579 A1 | 8/2002 | Kotoulas et al. | |
| 2002/0123078 A1 | 9/2002 | Seul et al. | |
| 2003/0015590 A1 | 1/2003 | Chen | |
| 2003/0039590 A1 | 2/2003 | Lodge | |
| 2003/0116630 A1 | 6/2003 | Carey et al. | |
| 2003/0143614 A1 | 7/2003 | Drmanac | |
| 2003/0205625 A1 | 11/2003 | Eilersen | |
| 2003/0233069 A1 | 12/2003 | Gillespie et al. | |
| 2004/0008853 A1 | 1/2004 | Pelrine et al. | |
| 2004/0024368 A1 | 2/2004 | Broselow | |
| 2004/0046032 A1 | 3/2004 | Urano et al. | |
| 2004/0051368 A1 | 3/2004 | Caputo et al. | |
| 2004/0141426 A1 | 7/2004 | Kawasaki et al. | |
| 2004/0155113 A1 | 8/2004 | Urano et al. | |
| 2004/0178255 A1 | 9/2004 | Eich et al. | |
| 2004/0200558 A1 | 10/2004 | Stevens et al. | |
| 2004/0207385 A1 | 10/2004 | Gafner et al. | |
| 2004/0210199 A1 | 10/2004 | Atterbury et al. | |

(56) References Cited

U.S. PATENT DOCUMENTS

| | | | |
|---|---|---|---|
| 2004/0243130 A1* | 12/2004 | Biscup | 606/73 |
| 2005/0006472 A1 | 1/2005 | Verschuur et al. | |
| 2005/0035207 A1 | 2/2005 | Philyaw et al. | |
| 2005/0060059 A1 | 3/2005 | Klein et al. | |
| 2005/0116033 A1 | 6/2005 | Moore | |
| 2005/0156318 A1 | 7/2005 | Douglas | |
| 2005/0182360 A1* | 8/2005 | Yeandel et al. | 604/96.01 |
| 2005/0236603 A1 | 10/2005 | Faris | |
| 2005/0283116 A1 | 12/2005 | Eakins et al. | |
| 2006/0097877 A1 | 5/2006 | Baba et al. | |
| 2006/0118612 A1 | 6/2006 | Christoffersen et al. | |
| 2006/0125491 A1 | 6/2006 | Grishin et al. | |
| 2006/0129104 A1 | 6/2006 | Cowan et al. | |
| 2006/0138233 A1 | 6/2006 | Kemppainen et al. | |
| 2006/0164002 A1 | 7/2006 | O'Brien et al. | |
| 2006/0170981 A1 | 8/2006 | Ricks et al. | |
| 2006/0175427 A1 | 8/2006 | Jonientz et al. | |
| 2006/0176267 A1 | 8/2006 | Honeyman et al. | |
| 2006/0224123 A1 | 10/2006 | Friedli et al. | |
| 2006/0226238 A1 | 10/2006 | Salib et al. | |
| 2006/0243804 A1 | 11/2006 | Christoffersen et al. | |
| 2007/0080234 A1 | 4/2007 | Domoy | |
| 2007/0239116 A1 | 10/2007 | Follman et al. | |
| 2008/0015510 A1 | 1/2008 | Sandoz et al. | |
| 2009/0088701 A1 | 4/2009 | Larsen | |

FOREIGN PATENT DOCUMENTS

| | | |
|---|---|---|
| DE | 1950411 | 11/1966 |
| DE | 2636634 | 2/1978 |
| DE | 3712089 | 10/1988 |
| DE | 4234016 | 4/1993 |
| DE | 4402319 | 8/1994 |
| DE | 19504111 | 8/1995 |
| DE | 19637967 | 9/1996 |
| DE | 19814687 | 2/1999 |
| DE | 10035192 | 10/2001 |
| EP | 235691 | 9/1987 |
| EP | 248165 | 12/1987 |
| EP | 336778 | 10/1989 |
| EP | 364010 | 4/1990 |
| EP | 398717 | 11/1990 |
| EP | 402553 | 12/1990 |
| EP | 492954 | 7/1992 |
| EP | 573129 | 12/1993 |
| EP | 588427 | 3/1994 |
| EP | 626660 | 11/1994 |
| EP | 685810 | 12/1995 |
| EP | 690457 | 1/1996 |
| EP | 716290 | 6/1996 |
| EP | 833273 | 4/1998 |
| EP | 833278 | 4/1998 |
| EP | 911859 | 4/1999 |
| EP | 1095668 A1 | 5/2001 |
| EP | 1142643 | 10/2001 |
| EP | 1143643 | 10/2001 |
| EP | 1193641 | 4/2002 |
| EP | 1246127 | 10/2002 |
| EP | 1462134 | 9/2004 |
| EP | 1503185 | 2/2005 |
| FR | 2771111 | 5/1999 |
| GB | 2088163 | 6/1982 |
| GB | 2159007 | 11/1985 |
| GB | 2216259 | 10/1989 |
| GB | 2287551 | 9/1995 |
| GB | 2309801 | 8/1997 |
| GB | 2336927 | 11/1999 |
| GB | 2341965 | 3/2000 |
| JP | 56-094475 | 7/1981 |
| JP | 59-131917 A | 7/1984 |
| JP | 62/239019 A | 10/1987 |
| JP | 63-100303 A | 5/1988 |
| JP | 2-85370 A | 3/1990 |
| JP | 2-188702 | 7/1990 |
| JP | 2-250083 | 10/1990 |
| JP | 3-27037 A | 2/1991 |
| JP | 4-222084 A | 8/1992 |
| JP | 4-233680 A | 8/1992 |
| JP | 4-233684 A | 8/1992 |
| JP | 5006449 | 1/1993 |
| JP | 5-500917 | 2/1993 |
| JP | 5-314296 | 11/1993 |
| JP | 6-163027 | 6/1994 |
| JP | 06-171194 | 6/1994 |
| JP | 6-333102 | 12/1994 |
| JP | 7-098752 | 4/1995 |
| JP | 7-271890 | 10/1995 |
| JP | 8-106648 | 4/1996 |
| JP | 8-118864 | 5/1996 |
| JP | 08/159704 A | 6/1996 |
| JP | 8-179475 | 7/1996 |
| JP | 8-220994 | 8/1996 |
| JP | 8-262980 | 10/1996 |
| JP | 9-16703 | 1/1997 |
| JP | 9-034361 | 2/1997 |
| JP | 9-091364 | 4/1997 |
| JP | 9-192220 | 7/1997 |
| JP | 9-223181 | 8/1997 |
| JP | 9-274637 | 10/1997 |
| JP | 10-105635 | 4/1998 |
| JP | 10-268777 | 10/1998 |
| JP | 11-135172 | 5/1999 |
| JP | 11-162591 | 6/1999 |
| JP | 11-180079 | 7/1999 |
| JP | 11-276583 | 10/1999 |
| JP | 11-316877 | 11/1999 |
| JP | 2000-040119 | 2/2000 |
| JP | 2000-272191 | 10/2000 |
| JP | 2001-043301 | 2/2001 |
| JP | 2001-075480 | 3/2001 |
| JP | 2002-082120 | 3/2002 |
| JP | 2002-517737 | 6/2002 |
| JP | 2004-535590 A | 11/2004 |
| JP | 4-233624 B2 | 12/2008 |
| WO | WO 91/04759 | 4/1991 |
| WO | WO 92/17231 | 10/1992 |
| WO | WO 93/12828 | 7/1993 |
| WO | WO 94/08647 | 4/1994 |
| WO | WO 94/12235 | 6/1994 |
| WO | 94/15120 | 7/1994 |
| WO | WO 95/24317 | 9/1995 |
| WO | WO 95/28190 | 10/1995 |
| WO | WO 99/60533 | 11/1999 |
| WO | WO 99/65548 | 12/1999 |
| WO | WO 00/42678 | 7/2000 |
| WO | WO 01/22348 | 3/2001 |
| WO | WO 01/54055 | 7/2001 |
| WO | WO 01/62322 | 8/2001 |
| WO | WO 01/70304 | 9/2001 |
| WO | WO 01/84542 | 11/2001 |
| WO | 0195959 | 12/2001 |
| WO | 0195959 A1 | 12/2001 |
| WO | WO 02/11792 | 2/2002 |
| WO | WO 02/13133 | 2/2002 |
| WO | 02/092153 | 11/2002 |
| WO | WO 02/092153 | 11/2002 |
| WO | WO 02/095675 | 11/2002 |
| WO | WO 03/017915 | 3/2003 |
| WO | WO 03/020598 | 3/2003 |
| WO | WO 03/038738 | 5/2003 |
| WO | 03103753 A1 | 12/2003 |
| WO | WO 2004/084795 | 10/2004 |
| WO | WO 2004/097715 | 11/2004 |
| WO | WO 2005/075010 | 8/2005 |
| WO | WO 2005/089835 | 9/2005 |
| WO | 2005/110387 | 11/2005 |
| WO | 2005/110387 A2 | 11/2005 |
| WO | 2006/113521 | 10/2006 |
| WO | 2006/113521 A2 | 10/2006 |
| WO | 2006/120182 | 11/2006 |
| WO | 2006/120182 A1 | 11/2006 |
| WO | WO 2007/039148 A1 | 4/2007 |
| WO | WO 2007/107562 | 9/2007 |

(56) References Cited

FOREIGN PATENT DOCUMENTS

| WO | WO 2007/116090 | 10/2007 |
|---|---|---|
| WO | WO 2007/122253 A1 | 11/2007 |
| WO | WO 2009/015933 | 2/2009 |

OTHER PUBLICATIONS

International Search Report for PCT/EP2006/009240, mailed Jan. 4, 2007.
English Language Abstract of German Patent No. DE19637967, published Sep. 18, 1996, obtained from espacenet.com database.
English Language Abstract of German Patent No. DE4234016, published Apr. 15, 1993, obtained from espacenet.com database.
English Language Abstract of German Patent No. DE4402319, published Aug. 4, 1994, obtained from espacenet.com database.
Japanese Office Action in Related Case Japanese Application No. 2002-518416 Filed Feb. 10, 2003.
JP 11-276583 English Abstract Oct. 12, 1999.
JP 06-171194 English Abstract Jun. 21, 1994.
JP 56-094475 English Abstract Jul. 30, 1981.
JP 5006449 English Abstract Jan. 14, 1993.
Non-Final Office Action Mailed Oct. 30, 2010 in U.S. Appl. No. 11/912,347, filed Oct. 23, 2007; First Named Inventor: Preben Mikael Nielsen.
Final Office Action Mailed Apr. 15, 2011 in U.S. Appl. No. 11/912,347, filed Oct. 23, 2007; First Named Inventor: Preben Mikael Nielsen.
Non-Final Office Action Mailed Sep. 29, 2010 in U.S. Appl. No. 12/293,251, filed Sep. 16, 2008; First Named Inventor: Andre Larsen.
Final Office Action Mailed Apr. 14, 2011 in U.S. Appl. No. 12/239,251, filed Sep. 16, 2008; First Named Inventor: Andre Larsen.
International Search Report for PCT/EP07/053558, mailed Jul. 23, 2007.
CN 1051152 English Abstract, Sep. 15, 1993.
CN 1013704 English Abstract, Aug. 28, 1991.
DE 19814687 Machine Translation, Feb. 18, 1999.
DE 19504111 Machine Translation, Aug. 10, 1995.
DE 10035192 Machine Translation, Oct. 11, 2001, DE 10035192 previously cited.
DE 3712089 English Abstract, Oct. 27, 1988.
DE 2636634 English Abstract, Feb. 16, 1978.
FR 2771111 Machine Translation, May 21, 1999.
JP 2002-517737 Machine Translation, Jun. 18, 2002.
JP 2002-082120 English Abstract, Mar. 22, 2002.
JP 2001-075480 English Abstract, Mar. 23, 2001.
JP 2001-043301 Machine Translation, Feb. 16, 2001.
JP 2000-040119 Machine Translation, Feb. 8, 2000.
JP 2000-272191 Machine Translation, Oct. 3, 2000.
JP 11-316877 Machine Translation Nov. 16, 1999.
JP 11-180079 Machine Translation, Jul. 6, 1999.
JP 11-162591 Machine Translation, Jun. 18, 1999.
JP 11-135172 Machine Translation, May 21, 1999.
JP 10-268777 Machine Translation, Oct. 9, 1998.
JP 10-105635 Machine Translation, Apr. 24, 1998.
JP 9-274637 Machine Translation, Oct. 21, 1997.
JP 9-223181 Machine Translation, Aug. 26, 1997.
JP 9-192220 Machine Translation, Jul. 29, 1997.
JP 9-091364 Machine Translation, Apr. 4, 1997.
JP 9-034361 Machine Translation, Feb. 7, 1997.
JP 9-16703 Machine Translation, Jan. 17, 1997.
JP 8-262980 Machine Translation, Oct. 11, 1996.
JP 8-220994 Machine Translation, Aug. 30, 1996.
JP 8-179475 Machine Translation, Jul. 12, 1996.
JP 8-118864 Machine Translation, May 14, 1996.
JP 8-106648 Machine Translation, Apr. 23, 1996.
JP 7-271890 Machine Translation, Oct. 20, 1995.
JP 7-098752 Machine Translation, Apr. 11, 1995.
JP 6-333102 Machine Translation, Dec. 2, 1994.
JP 63-100303A English Abstract, May 2, 1988.
JP 6-163027 Machine Translation, Jun. 10, 1994.
JP 59-131917 English Abstract, Jul. 28, 1984.
JP 5-314296 Machine Translation, Nov. 26, 1993.
JP 5-500917 English Abstract, Feb. 25, 1993.
JP 4-233684A English Abstract, Aug. 21, 1992.
JP 4-233680A English Abstract, Aug. 21, 1992.
JP 4-233624B2 Machine Translation, Dec. 19, 2008.
JP 4-222084 English Abstract, Aug. 12, 1992.
JP 3-27037A English Abstract, Feb. 5, 1991.
JP 2-250083 English Abstract, Oct. 5, 1990.
JP 2-188702 English Abstract, Jul. 24, 1990.
JP 2-85370 English Abstract, Mar. 26, 1990.
WO 01/22348 English Abstract, Mar. 29, 2001.
Non-Final Office Action mailed Jan. 4, 2008 in U.S. Appl. No. 11/396,889, filed Apr. 3, 2006 by Christoffersen et al.
Notice of Allowance mailed Sep. 17, 2009 in U.S. Appl. No. 11/296,991, filed Dec. 8, 2005 by Eilersen et al.
Notice of Allowance mailed Apr. 30, 2009 in U.S. Appl. No. 11/296,991, filed Dec. 8, 2005 by Eilersen et al.
Non-Final Office Action mailed Oct. 14, 2008 in U.S. Appl. No. 11/296,991, filed Dec. 8, 2005 by Eilersen et al.
Corrected Notice of Allowance mailed Jun. 19, 2009 in U.S. Appl. No. 11/232,469, filed Sep. 19, 2005 by Christoffersen et al.
Notice of Allowance mailed Jun. 8, 2009 in U.S. Appl. No. 11/232,469, filed Sep. 19, 2005 by Christoffersen et al.
Non-Final Office Action mailed Dec. 17, 2008 in U.S. Appl. No. 11/232,469, filed Sep. 19, 2005 by Christoffersen et al.
Final Office Action mailed Jul. 2, 2008 in U.S. Appl. No. 11/232,469, filed Sep. 19, 2005 by Christoffersen et al.
Non-Final Office Action mailed Jan. 3, 2008 in U.S. Appl. No. 11/232,469, filed Sep. 19, 2005 by Christoffersen et al.
Non-Final Office Action mailed Jun. 19, 2007 in U.S. Appl. No. 11/232,469, filed Sep. 19, 2005 by Christoffersen et al.
Non-Final Office Action mailed Oct. 23, 2003 in U.S. Appl. No. 10/463,915, filed Jun. 18, 2003 by Eilersen et al.
Non-Final Office Action mailed Apr. 15, 2004 in U.S. Appl. No. 10/463,915, filed Jun. 18, 2003 by Eilersen et al.
Notice of Allowance mailed Aug. 16, 2004 in U.S. Appl. No. 10/463,915, filed Jun. 18, 2003 by Eilersen et al.
Notice of Allowance mailed Aug. 13, 2003 in U.S. Appl. No. 09/925,995, filed Aug. 9, 2001 by Eilersen et al.
Non-Final Office Action mailed Nov. 12, 2002 in U.S. Appl. No. 09/925,995, filed Aug. 9, 2001 by Eilersen et al.
Notice of Allowance mailed Aug. 11, 2005 in U.S. Appl. No. 09/925,792, filed Aug. 9, 2001 by Eilersen et al.
Non-Final Office Action mailed Apr. 4, 2005 in U.S. Appl. No. 09/925,792, filed Aug. 9, 2001 by Eilersen et al.
Notice of Allowance mailed Oct. 8, 2002 in U.S. Appl. No. 09/846,799, filed May 1, 2001 by Aasmul et al.
Non-Final Office Action mailed May 8, 2002 in U.S. Appl. No. 09/846,799, filed May 1, 2001 by Aasmul et al.

* cited by examiner a)

b)

US 8,994,382 B2

ABSOLUTE POSITION DETERMINATION OF MOVABLY MOUNTED MEMBER IN MEDICATION DELIVERY DEVICE

CROSS-REFERENCE TO RELATED APPLICATIONS

This application is a 35 U.S.C. §371 national stage application of International Patent Application PCT/EP2007/053558 (published as WO 2007/116090), filed Apr. 12, 2007, which claimed priority of European Patent Application 06007633.8, filed Apr. 12, 2006; this application further claims priority under 35 U.S.C. §119 of U.S. Provisional Application 60/796,099, filed Apr. 28, 2006.

FIELD OF THE INVENTION

The present invention relates to a method and a medication delivery device comprising an assembly for determining an absolute position of a movably mounted member in the medication delivery device. In particular, the present invention relates to a method and a medication delivery device comprising an assembly for determining an angular position of a rotatably mounted dose indication barrel in the medication delivery device. The assembly according to the present invention takes up a minimum amount of space.

BACKGROUND OF THE INVENTION

U.S. Pat. No. 4,420,754 discloses a system for measuring the relative movement between two elements, such as the scale and slide of a hand-held measuring instrument. The system includes the provision of a number of groups of supply electrodes on the slide, each of the electrodes in each group being supplied from a respective one of a multiple number of output signals from a signal generator so that all of the supply electrodes are furnished with voltages according to a cyclic pattern, the slide also having at least one receiving electrode which feeds a signal processing unit. The scale is provided with an electronic pattern comprising internally galvanically connected parts, one being a detecting part, located close to the area where the supply electrodes of the slide are moved, the other of the two parts being a transferring part which is located close to the area where the receiving electrode of the slide is moved. The movement of the slide along the scale generates a signal from the receiving electrode which is derived from the signals from at least two adjacent supply electrodes and the position of the slide is determined by a signal processing unit which identifies the amplitude ratio of the received signals.

U.S. Pat. No. 6,329,813 discloses an inductive absolute position sensor applying at least one magnetic field generator that generates a first changing magnetic flux in a first flux region. A plurality of coupling loops have a first plurality of coupling loop portions spaced at an interval related to a first wavelength along a measuring axis and a second plurality of coupling loop portions spaced at an interval related to a second wavelength along a measuring axis. One of the first plurality of coupling loop portions and the second plurality of coupling loop portions are inductively coupled to a first changing magnetic flux from a transmitter winding in a first flux region to generate a second changing magnetic flux outside the first flux region in the other of the first plurality of coupling loop portions and the second plurality of coupling loop portions. A magnetic flux sensor is positioned outside the first flux region and is responsive to the second changing magnetic flux to generate a position-dependent output signal. The output signal varies at the first or second wavelength of the corresponding other of the first plurality of coupling loop portions and the second plurality of coupling loop portions that generates the second changing magnetic flux.

The arrangements suggested in both U.S. Pat. Nos. 4,420,754 and 6,329,813 are adapted for determining linear translations between two objects.

US 2004/0207385 relates to a device for contact free detection of a position of a rotor relative to a stator, where at least one electrode is arranged on the rotor and at least one electrode is arranged on the stator. The electrodes overlap in at least one rotational position of the rotor relative to the stator. US 2004/0207385 further relates to a corresponding method for measuring the rotational position of a rotor relative to a stator. The rotational position is detected using a capacitive coupling between the rotor electrode and the stator electrode.

US 2004/0207385 relates to contact free determination of angular positions between two objects such as between a rotatably mounted rotor and a stationary stator. It is a disadvantage of the arrangement suggested in US 2004/0207385 that the emitters and receivers are position in a manner where they take up an unnecessary amount of space. For compact systems the solution suggested by US 2004/0207385 is not applicable.

WO 02/092153 relates to a medication injector apparatus with various arrangements for position determination. The arrangement depicted in FIG. 20 of WO 02/092153 is constituted by an electrically conducting matrix where six horizontally oriented rows are connected by vertically oriented matrix elements. The six horizontally oriented rows and the vertically oriented matrix elements constitute an integrated electrically conducting matrix.

U.S. Pat. No. 5,986,585 relates to a device for converting mechanical deflections into corresponding electrical variables. Two pairs of contact terminals are moveably arranged relative to two groups of contact pads where driving signals are provided to one of said groups. One or more output signals are retrieved from one or more electrodes of the second group—said one or more output signals being indicative of the position of the contact terminals relative to the two groups of contact pads. The arrangement suggested in U.S. Pat. No. 5,986,585 is not suitable for measuring angular positions between two elements.

It is an object of the present invention to provide a space saving arrangement for measuring absolute position of a first member, such as a dose indicator barrel, relative to a second member, such as a housing of a medication delivery device.

SUMMARY OF THE INVENTION

The above-mentioned object is complied with by providing, in a first aspect, a medication delivery device comprising a position determining assembly for determining absolute positions of a first member relative to a second member of the medication delivery device, the position determining assembly comprising first and second electrically conducting electrodes arranged on the first member, wherein the first and second electrically conducting electrodes are electrically connected through an electronic device having a measurable electronic value, and wherein the first and second electrically conducting electrodes form part of a first group of electrodes, first and second contact members being adapted to establish galvanic electrical connections to the first and second electrically conducting electrodes, said first and second contact members further being adapted to be slided across the first and second electrically conducting electrodes when the first member is moved relative the second member, and an electronic control circuit electrically coupled to the first and second contact members, the electronic control circuit being adapted to determine the measurable electronic value of the electronic device, the electronic control circuit further being adapted to compare a determined measurable electronic value with a set of predetermined values.

The first and second members may in principle be any members or parts of the medication delivery device. Thus, the first member may be a moveably mounted member, such as for example a rotatably mounted member, relative to the second member. The movably mounted member may be a dose indicator barrel being arranged to rotate during setting of a dose of medicament to be expelled from the medication delivery device. The dose indicator barrel may be arranged to perform a combined rotational and translational movement so that a point on the dose indicator barrel follows a substantially helical path during setting of a dose of medicament to be expelled from the medication delivery device.

The movably mounted member may also be a piston rod adapted to be displaced along an axial direction of the medication delivery device. This displacement may be provided by a translational movement of the piston rod, or a combined rotational/translational movement of the piston rod.

In a preferred embodiment of the present invention the first member forms part of the dose indicator barrel whereas the second member forms part of a housing of the medication delivery device.

The first and second electrically conducting electrodes may be metallic electrodes arranged on an outer surface part of the first member. However, other externally accessible surfaces are also applicable.

The first group of electrodes may comprise additional electrically conducting electrodes being connected through respective electronic devices each having a measurable electronic value. Thus, between two given electrically conducting electrodes an electronic device having a measurable electronic value, such as a resistance, capacitance, inductance etc., is provided.

The medication delivery device may further comprise a second group of electrically conducting electrodes being connected through respective electronic devices each having a measurable electronic value, such as a resistance, capacitance, inductance etc. Third and fourth contact members may be provided for establishing galvanic electrical connections to electrically conducting electrodes of the second group. These third and fourth contact members may be adapted to be slided across electrically conducting electrodes of the second group when the first member is moved relative to the second member.

In a preferred embodiment of the present invention the assembly comprises four contact members arranged in a 2×2 matrix where two (first and second contact members) of the four contact members follow a first path or route across electrodes of the first group. The remaining two contact members (third and fourth contact members) follow a second path or route across electrodes of the second group. Thus, according to this preferred embodiment of the present invention pairs of contact members follow the same path or route on the first member.

The total number of contact members may be increased. Thus, pairs of contact members may follow three, four, five or even more different paths or routes on the first member. Also, the number of contact members following the same path or route may be increased from two.

The electrically conducting electrodes of each of the first and second groups of electrodes may be arranged in a periodic structure along a predetermined direction. This predetermined direction may be the direction along which the first and second members are moved relative to each other. The shape of the electrically conducting electrodes may also vary. Thus, a number of the electrically conducting electrodes may have a linear shape, whereas other electrically conducting electrodes may a more complicated structure, such as a structure having essentially orthogonal components. Such essentially orthogonal components may be arranged in the direction along which the first and second members are moved relative to each other and orthogonal thereto.

The first member may be adapted to perform a translational movement relative to the second member. Alternatively, the first member may be adapted to perform a rotational movement relative to the second member. Alternatively, the first member may be adapted to perform a combined rotational and translational movement relative to the second member.

The electronic devices connecting the electrically conducting electrodes may comprise a number of resistors. Alternatively or in addition, the electronic devices connecting the electrically conducting electrodes may comprise a number of capacitors. Alternatively or in addition the electronic devices connecting the electrically conducting electrodes may comprise a number of inductors.

The contact members may be mechanically biased towards the first member. In this way proper electrical connections are provided between the contact members and the electrically conducting electrodes arranged on the first member. Preferably, the contact members are arranged in a fixed relationship with a housing of the medication delivery device.

Preferably, the first member forms part of a rotatably mounted dose indicator barrel arranged within the housing of the medication delivery device.

In a second aspect the present invention relates to a method for determining absolute positions of a first member relative to a second member of a medication delivery device, the method comprising the steps of providing first and second electrically conducting electrodes arranged on the first member, wherein the first and second electrically conducting electrodes are electrically connected through an electronic device having a measurable electronic value, and wherein the first and second electrically conducting electrodes form part of a first group of electrodes, providing first and second contact members being adapted to establish galvanic electrical connections to the first and second electrically conducting electrodes, said first and second contact members further being adapted to be slided across the first and second electrically conducting electrodes when the first member is moved relative to the second member, and determining the measurable electronic value of the electronic device, and comparing the determined measurable electronic value with a set of predetermined values.

As previously mentioned, the first and second members may in principle be any members or parts of the medication delivery device. Thus, the first member may be a moveably mounted member, such as for example a rotatably mounted member, relative to the second member. The movably mounted member may be a dose indicator barrel being arranged to rotate during setting of a dose of medicament to be expelled from the medication delivery device. The dose indicator barrel may also be arranged to perform a combined rotational and translational movement so that a point on the dose indicator barrel follows a substantially helical path during setting of a dose of medicament to be expelled from the medication delivery device.

The movably mounted member may also be a piston rod adapted to be displaced along an axial direction of the medication delivery device. This displacement may be provided by a translational movement of the piston rod, or a combined rotational/translational movement of the piston rod.

In a preferred embodiment of the present invention the first member forms part of the dose indicator barrel whereas the second member forms part of a housing of the medication delivery device. In this situation the first and second electrically conducting electrodes may be arranged on an outer surface part of the first member—here an outer surface of the dose indicator barrel.

The determining of the measurable electronic value and the comparison of the determined measurable electronic value with a set of predetermined values may be performed by an electronic control circuit integrated in the medication delivery device, The method according to the second aspect of the present invention may further comprise the steps of determining additional measurable electronic values of respective ones of additional electronic devices connecting additional electrically conducing electrodes of the first group, and comparing the determined additional measurable electronic values with the set of predetermined values. Thus, between two given electrically conducting electrodes an electronic device having a measurable electronic value, such as a resistance, capacitance, inductance etc., is provided.

The method according to the present invention may further comprise the step of providing third and fourth contact members being adapted to establish galvanic electrical connections to electrically conducting electrodes of a second group, said third and fourth contact members further being adapted to be slided across electrically conducting electrodes of the second group when the first member is moved relative to the second member. The method may further comprise the steps of determining measurable electronic values of respective ones of electronic devices connecting electrically conducing electrodes of the second group of electrodes, and comparing the determined measurable electronic values with a set of predetermined values.

The predetermined values may be arranged in a look-up table. The measured electronic value(s) may be compared to values in the look-up table in the following manner: Firstly, the first measured value is looked for in the look-up table. When a match has been found, a second measured value (measured at the same position) in looked for in the look-up table. This sequence of comparisons is continued until all measured values associated with a given position have been matched will values in the look-up table, or until the look-up table contains no further values to be compared with.

As stated above, a preferred embodiment of the present invention relates to an assembly comprising four contact members arranged in a 2×2 matrix where two (first and second contact members) of the four contact members follow a first path or route across electrodes of the first group. The remaining two contact members (third and fourth contact members) follow a second path or route across electrodes of the second group. Thus, according to this preferred embodiment of the present invention pairs of contact members follow the same path or route on the first member.

The determined measurable electronic values may comprise a resistance, a capacitance, an inductance or a combination thereof.

The first member may be adapted to perform a translational movement, a rotational movement or a combination thereof relative to the second member.

The contact members may be mechanically biased towards the first member. In this way proper electrical connections are provided between the contact members and the electrically conducting electrodes arranged on the first member. Preferably, the contact members are arranged in a fixed relationship with a housing of the medication delivery device.

Preferably, the first member forms part of a rotatably mounted dose indicator barrel arranged within the housing of the medication delivery device.

In a third aspect the present invention relates to a position determining assembly for determining absolute positions of a first member relative to a second member of the medication delivery device, the position determining assembly comprising first and second electrically conducting electrodes arranged on the first member, wherein the first and second electrically conducting electrodes are electrically connected through an electronic device having a measurable electronic value, and wherein the first and second electrically conducting electrodes form part of a first group of electrodes, first and second contact members being adapted to establish galvanic electrical connections to the first and second electrically conducting electrodes, said first and second contact members further being adapted to be slided across the first and second electrically conducting electrodes when the first member is moved relative the second member, and an electronic control circuit electrically coupled to the first and second contact members, the electronic control circuit being adapted to determine the measurable electronic value of the electronic device, the electronic control circuit further being adapted to compare a determined measurable electronic value with a set of predetermined values.

In terms of implementation the position determining assembly according to the third aspect of the present invention may be configured along the lines suggested in connection with the first and second aspects of the present invention.

Thus, the first group of electrodes may comprise additional electrically conducting electrodes being connected through respective electronic devices each having a measurable electronic value. Thus, between two given electrically conducting electrodes an electronic device having a measurable electronic value, such as a resistance, capacitance, inductance etc., is inserted.

In addition, the position determining assembly may further comprise a second group of electrically conducting electrodes being connected through respective electronic devices each having a measurable electronic value, such as a resistance, capacitance, inductance etc. Third and fourth contact members may be provided for establishing galvanic electrical connections to electrically conducting electrodes of the second group. These third and fourth contact members may be adapted to be slided across electrically conducting electrodes of the second group when the first member is moved relative to the second member.

In a preferred embodiment, the position determining assembly comprises four contact members arranged in a 2×2 matrix where two (first and second contact members) of the four contact members follow a first path or route across electrodes of the first group. The remaining two contact members (third and fourth contact members) follow a second path or route across electrodes of the second group. Thus, according to this preferred embodiment of the present invention pairs of contact members follow the same path or route on the first member.

In a fourth aspect the present invention relates to a medication delivery device for expelling set doses of medicament, the medication delivery device comprising a position determining arrangement for detecting absolute positions of a movably mounted member arranged within the device relative to a housing of the medication delivery device, the position determining arrangement comprising a plurality of electrically conducting electrodes arranged on an outer surface of the movably mounted member, said plurality of electrically conducting electrodes being inter-connected through a number of electronic devices, and a plurality of contacts members fixedly arranged relative to the housing of the medication delivery device, each contact member being adapted to establish an electrical connection to the plurality of electrically conducting electrodes, each contact member further being adapted to be slid across the plurality of the electrically conducting electrodes while the movably mounted member is moved relative to the housing of the medication delivery device, wherein a first and a second contact member are arranged to follow a first path across the electrically conducting electrodes upon movement of the movably mounted member relative to the housing, and wherein a third and a fourth contact member are arranged to follow a second path across the electrically conducting electrodes upon movement of the movably mounted member relative to the housing.

The movably mounted member may in principle be any member within the medication delivery device. Thus, the movably mounted member may be a dose indicator barrel being arranged to rotate during setting of a dose of medicament to be expelled from the medication delivery device. The dose indicator barrel may also be arranged to perform a combined rotational and translational movement so that a point on the dose indicator barrel follows a substantially helical path during setting of a dose of medicament to be expelled from the medication delivery device.

The movably mounted member may also be a piston rod adapted to be displaced along an axial direction of the medication delivery device. This displacement may be provided by a translational movement of the piston rod, or a combined rotational/translational movement of the piston rod.

Thus, the movably mounted member may be adapted to perform a translational movement relative to the housing of the medication delivery device. Alternatively, the movably mounted member may be adapted to perform a rotational movement relative to the housing of the medication delivery device. Even further, the movably mounted member may be adapted to a combined rotational and translational movement relative to the housing of the medication delivery device.

The electronic devices inter-connecting the electrically conducting electrodes may comprise a number of resistors, a number of capacitors, a number of inductors or a combination thereof.

In a preferred embodiment of the present invention the arrangement comprises four contact elements arranged in a 2×2 matrix where two of the four contact members follow a first path or route on the movably mounted member. The remaining two contact members follow a second path or route on the movably mounted member. Thus, according to this preferred embodiment pairs of contact members follow the same path or route on the movably mounted member.

The total number of contact members may be increased. Thus, pairs of contact members may follow three, four, five or even more different paths or routes on the movably mounted member. Also, the number of contact members following the same path or route may be increased from two.

In order to provide proper electrical contact to the plurality of electrodes arranged on a surface of the movably mounted member the plurality of contact members may advantageously be mechanically biased towards the movably mounted member. This mechanical biasing may be provided by various means, such as spring, resilient blades etc.

The medication delivery device according to the fourth aspect of the present invention may further comprise an electronic control circuit electrically coupled to the plurality of contact members, the electronic control circuit being adapted to measure an electrical parameter between pairs contact members. The electrical parameter may be of resistive, capacitive or inductive nature.

In a fifth aspect, the present invention relates to a method for determining absolute positions of a movably mounted member arranged within a medication delivery device relative to a housing of the medication delivery device, the method comprising the steps of providing a plurality of electrically conducting electrodes on an outer surface of the movably mounted member, said plurality of electrically conducting electrodes being inter-connected through a number of electronic devices, providing a plurality of contacts members fixedly arranged relative to the housing of the medication delivery device, each contact member being adapted to establish an electrical connection to the plurality of electrically conducting electrodes, each contact member further being adapted to be slid across the plurality of the electrically conducting electrodes while the movably mounted member is moved relative to the housing of the medication delivery device, wherein a first and a second contact member are arranged to follow a first path across the electrically conducting electrodes upon movement of the movably mounted member relative to the housing, and wherein a third and a fourth contact member are arranged to follow a second path across the electrically conducting electrodes upon movement of the movably mounted member relative to the housing, and measuring a first electrical parameter between two contact members, said first electrical parameter being associated with a first electronic device.

The method may further comprise the steps of measuring second, third and fourth electrical parameters between pairs of contact members, said second, third and fourth electrical parameters being associated with second, third and fourth electronic devices, respectively. Thus, the electrical parameters may be of resistive, capacitive or inductive nature.

The method may further comprise the step of comparing the measured electrical parameter(s) with one or more predetermined values, said one or more predetermined values being arranged in a look-up table. The measured electrical parameter(s) may be compared to values in the look-up table in the following manner: Firstly, the first measured parameter is looked for in the look-up table. When a match has been found, a second measured parameter (measured at the same position) in looked for in the look-up table. This sequence of comparisons is continued until all measured parameters associated with a given position have been matched will values in the look-up table, or until the look-up table contains no further values to be compared with.

In a sixth aspect, the present invention relates to a position determining arrangement for detecting absolute positions of a movably mounted member arranged within a medication delivery device, the absolute position of the movably mounted member being determined relative to a housing of the medication delivery device, the position determining arrangement comprising a plurality of contacts members fixedly arranged relative to the housing of the medication delivery device, wherein first and second contact members are arranged to follow a first path across electrically conducting electrodes arranged on the movably mounted member, and wherein third and fourth contact members are arranged to follow a second path across electrically conducting electrodes arranged on the movably mounted member.

In a preferred embodiment the arrangement comprises four contact members arranged in a 2×2 matrix where two of the four contact members follow a first path or route on the movably mounted member. The remaining two contact members follow a second path or route on the movably mounted member. Thus, according to this preferred embodiment pairs of contact members follow the same path or route on the movably mounted member.

The total number of contact members may be increased. Thus, pairs of contact members may follow three, four, five or even more different paths or routes on the movably mounted member. Also, the number of contact members following the same path or route may be increased from two.

BRIEF DESCRIPTION OF THE DRAWINGS

The present invention will now be explained with reference to the accompanying figures, wherein.

Figure 1:
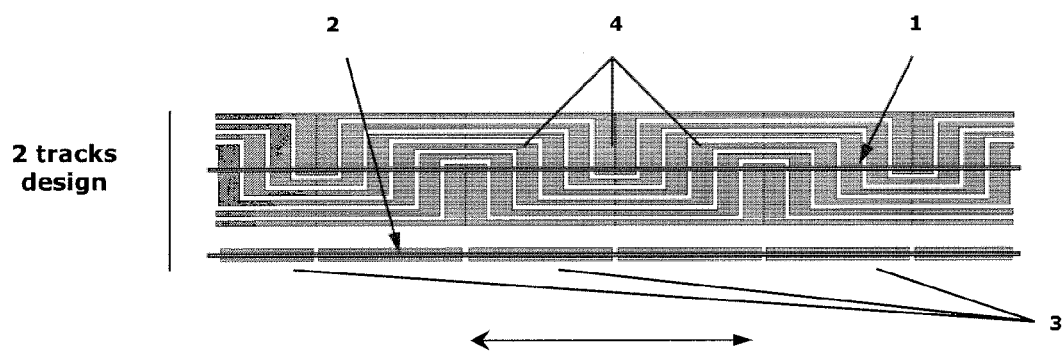
FIG. 1 shows a 3 and a 2 track design.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its broadest aspect the present invention relates to a medication delivery device comprising an assembly or an arrangement for determining the absolute position of a first member, such as a rotatably mounted dose indicator barrel, relative to a second member, such as a housing of the medication delivery device.

The assembly/arrangement is implemented to take up minimum space within the medication delivery device. This may be achieved by having two pairs of electrical contact members arranged so that a first pair of contact members follow a first path across an exterior surface of for example a the dose indicator barrel when said barrel is rotated relative to the housing, and where a second pair of contact members follow a second, and different, path across an exterior surface of the dose indicator barrel when said barrel is rotated relative to the housing. Thus, since the four contacts are arranged in a 2×2 matrix-like configuration the physical extension of the arrangement according to the present invention is significantly smaller compared to prior art systems.

Referring now to FIG. 1 a possible solution according to the present invention is depicted—the direction of movement between the first and second members of the medication delivery device is indicated by the arrow. The arrangement shown in FIG. 1 relies on resistor encoding. However, capacitive or inductive encoding may be applied as well.

FIG. 1 shows an arrangement applying two paths 1, 2—FIG. 1 is simplified in that no connections between the six bottom electrodes 3 are shown. Also, no connections between the ends of the six electrodes 4 (below path 1) are shown. The total number of metal electrodes is 12 and the number of resistors (not shown) is nine.

As mentioned above, the decoding relies on measuring the resistance between four individual contact members. The change in resistance originates from the four contact members being in electrical contact with the 12 metallic electrodes. The 12 metallic electrodes are interconnected with nine resistors having values that make them distinguishable from each other. The resistances of these nine resistors are in the range from 1 k$\Omega$ to 33 k$\Omega$ leading to current sources in the range 50 µA and 200 µA if voltages between 0 and 5V are applied.

Figure 2:
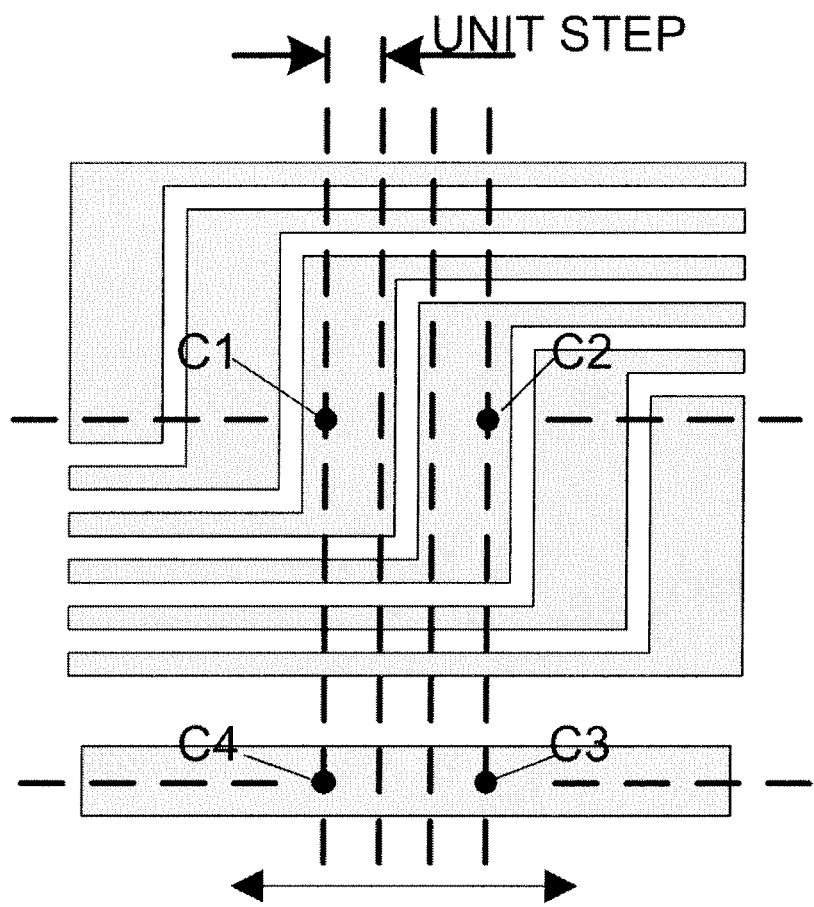
FIG. 2 shows the arrangement of four contacts according to the present invention.

Referring now to FIG. 2, four contact points, C1, C2, C3 and C4, and the electrodes on the exterior surface of for example a dose indicator barrel are shown. Again the arrow indicates the direction of movement between contact members and electrodes. The vertical lines running through the contact points are separated by three unit steps. Thus, whenever a movement occurs exactly one contact is displaced from one metallic electrode to another. In FIG. 2 only the top row of contact points will move from one electrode to another electrode whereas the bottom row of contact points remains on the same metal electrode. However, as movement progress the bottom row of contact points will move to adjacent electrodes.

Figure 3:
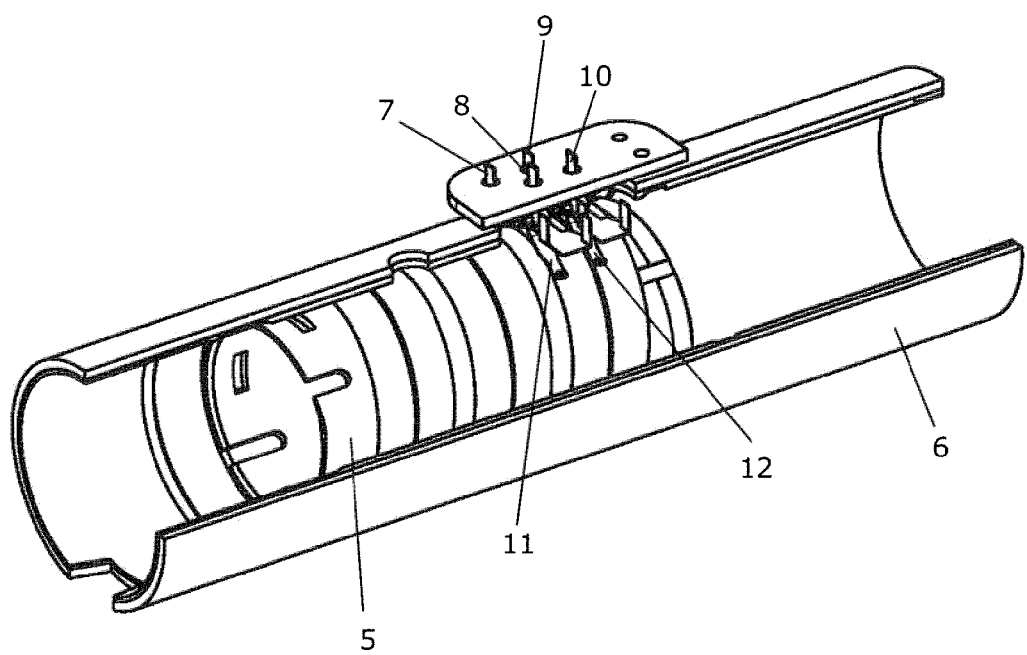
FIG. 3 shows the positioning of the four contacts in a medication delivery device.

FIG. 3 shows a dose indicator barrel 5 positioned in the housing 6 of a medication delivery device. The four contact members (only two 11, 12 are visible in FIG. 3) are electrically accessible via terminals 7, 8, 9 and 10. Upon rotation of the dose indication barrel 5 within the housing 6 the dose indicator barrels will perform a combined rotational/translational movement relative to the housing 6. Thus, a point on the surface of the dose indicator barrel 5 will follow a substantially helical path during such a rotational/translational movement. The dose indicator barrel is allowed to rotate at least 720 degrees.

As four contact members are available, six individual measurements between contact members are possible. At intermediate positions between full unit steps precisely one contact member is isolated. This reduces the number of meaningful measurements to three. In the present scheme only full positions are unique (requiring only four measurements), whereas the half-positions are not all clearly distinguishable from each other.

Position determining measurements can be implemented in various ways, but one very simple method is the following: If the contact members are numbered C1 to C4 (see FIG. 2) four combinations of measurements are selected for each position, namely C4-C3, C1-C2, C3-C2 and C4-C1.

Figure 4:
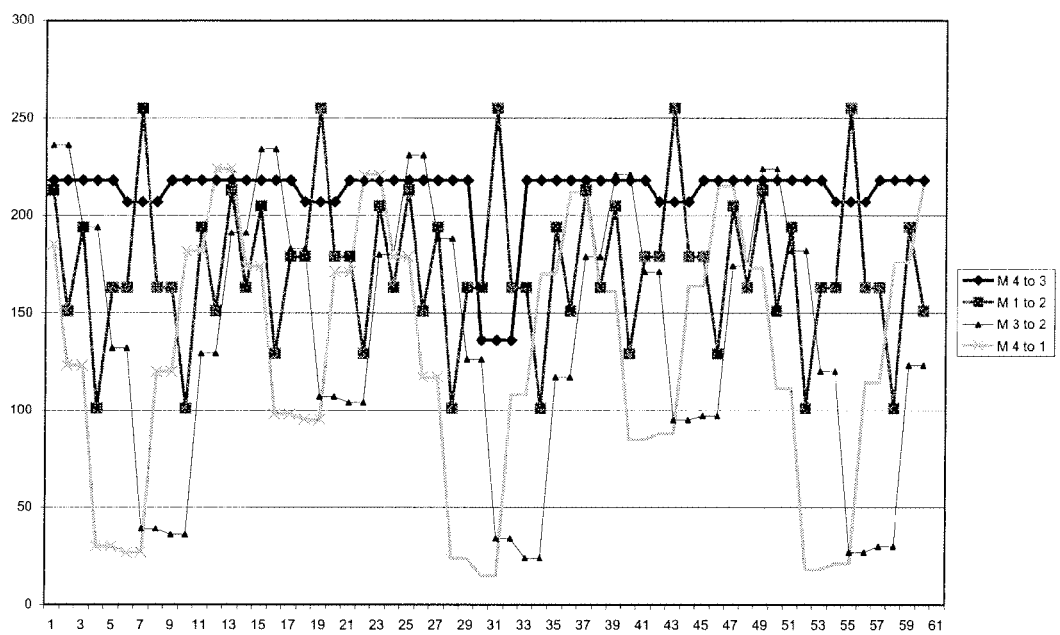
FIG. 4 shows 8-bit data for 61 positions.

FIG. 4 shows the resulting 8-bit ADC readings based on the above-mentioned four measurements for positions 0 to 60 (here numbered 1 to 61). In order to link these four measurements to positions a look-up table (LUT) is used. The look-up procedure can be as follows: When the first measurement, for example C4-C3, has been performed, this measurement is used to find a position in the LUT having a similar first measurement. If it is found, the second measurement is compared to the LUT. If all four measurements match, the position is uniquely identified.

Due to mechanical tolerances a complete match between a measurement and a value in the look-up table may not be reached. Thus, a match may be considered reached when the difference between the measurement and the LUT-value falls within a predetermined range of values. This range can be ±1% of the full measurement range.

In order to guard against erroneous readings several additional checks can be implemented as well. For example, a new position is not acknowledged before it has been read at least twice. Many different look-up procedures may be considered. For example, the last found position may be used as a starting point when looking for the next position. If a half-unit step is detected several actions can be taken. One strategy could be that if the half-unit step can be identified as a neighbor to the last known full-unit step the position associated with this last known full-unit step is used.

Figure 5:
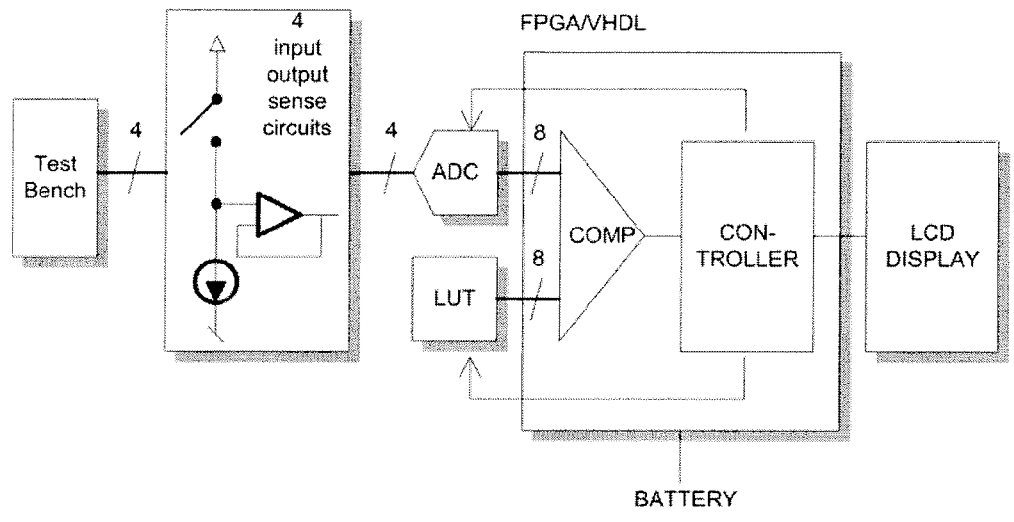
FIG. 5 shows block diagrams of sensing circuits.
Figure 5:
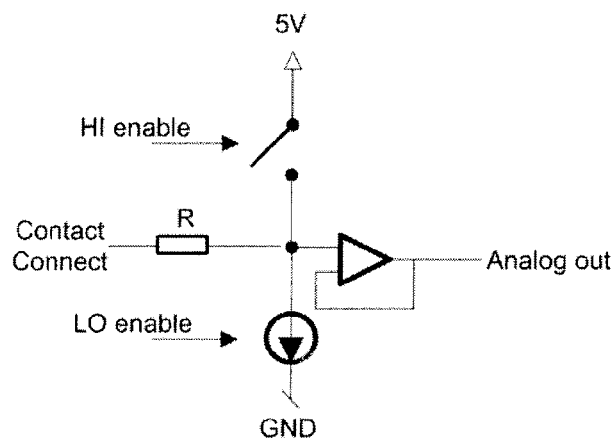

FIG. 5a shows block diagrams of the electronic system. The test bench is the above-described circuit of sliding contact members across metallic electrodes arranged on the exterior surface of the dose indicator barrel. Each of the four contact members is connected by a wire to the electronic system. Each wire is connected to four identical input-output sensing circuits. One of these input-output sensing circuits is shown in greater detail in FIG. 5b. As seen in FIG. 5b each input-output sensing circuit is connected to a contact and provides an analog output signal. The circuit has two control inputs which control whether the contact is driven high, driven low or not driven. Even if both inputs are enabled no problematic short circuit occurs.

In normal operation two contacts are connected through their respective input-output sensing circuits—one contact is driven high whereas the other is driven low. The analog output voltage of the driven low contact will when equal:

$$V_{out}=5V-I\times(R_{IO}+R_{ENC})$$

where $R_{IO}$ and $R_{ENC}$ are the resistances of the sensing resistor and the specific resistor between two electrodes, respectively. I is the current source of the sense circuit. As seen in FIG. 5a, the output voltages from the four sensing circuits are all fed to a 4-input Analog-to-Digital Converter (ADC).

The assembly according to the present invention may alternatively be configured as a simple counter where one count corresponds to a displacement of one unit step as illustrated in FIG. 2. The widths of the vertically arranged electrode elements in FIG. 2 (parallel to the dashed lines illustrating a unit step) need to be reduced by a factor of around two in order for this to work properly. With such a width reduction contact points C1 and C2 move from one electrode to a neighbouring electrode at a displacement of one unit step. This configuration allows absolute position determination within one period of the upper electrode pattern of FIG. 2.

The invention claimed is:

1. A medication delivery device comprising:
    a first device member and a second device member, the first device member moving relative to the second device member;
    a position determining assembly to determine the absolute positions of the first device member relative to the second device member;
    said first device member comprising first and second electrically conducting electrodes forming a first group of electrodes third and fourth electrically conduction electrodes forming a second group of electrodes, each having a measurable electronic value wherein said first group and said second group are arranged on an outer surface part of the first device member;
    said second device member comprising first and second contact members arranged on the second device member, the first and second contact members being adapted to establish galvanic electrical connections to respective ones of electrically conducting electrodes of the first group of electrodes and third and fourth contact members arranged on the second device member, the third and fourth contact members being adapted to establish galvanic electrical connections to respective ones of electrically conducting electrodes of the second group of electrodes, said first and second contact members further being adapted to slide across the first group of electrodes and said third and fourth contact members being adapted to slide across the second group of electrodes, when the first device member is moved relative the second device member so that the contact members galvanically connect to respective ones of said electronic devices as the first device member is moved relative to the second device member;
    wherein said electrodes and said contract members comprise two pairs of electrical contact members arranged so that said first pair of contact members follows a first path across the exterior surface of a first device member, when said first device member moves relative to said second device member, and said second pair of electrical contact members follow a second and different path across the exterior surface of said first device member, when said first device member moves relative to said second device member; and
    an electronic control circuit being adapted to determine the measurable electronic value of respective electronic devices between the contact members, wherein said determining relies on measuring the resistance between the four individual contact members, the electronic control circuit further being adapted to compare a determined measurable electronic value with a set of predetermined values to uniquely identify the position of the first device member relative to the second device member.

2. A medication delivery device according to claim 1, wherein the first device member forms part of a movably mounted member arranged within a housing of a medication delivery device.

3. A medication delivery device according claim 1, wherein the second device member forms part of a housing of a medication delivery device.

4. A medication delivery device according to claim 1, wherein the electrically conducting electrodes of each of the first and second groups of electrodes are arranged in a periodic structure along a predetermined direction.

5. A medication delivery device according to claim 1, wherein the first device member is adapted to perform a translational movement relative to the second device member.

6. A medication delivery device according to claim 1, wherein the first device member is adapted to perform a rotational movement relative to the second device member.

7. A medication delivery device according to claim 1, wherein the first device member is adapted to perform a combined rotational and translational movement relative to the second device member.

8. A medication delivery device according to claim 1, wherein the electronic devices connecting the electrically conducting electrodes comprise a number of resistors.

9. A medication delivery device according to claim 1, wherein the contact members are mechanically biased towards the first device member.

10. A medication delivery device according to claim 1, wherein the contact members are arranged in a fixed relationship with a housing of the medication delivery device.

11. A medication delivery device according to claim 1, wherein the first device member forms part of a rotatably mounted dose indicator barrel.

12. The medication delivery device according to claim 1, further comprising additional pairs of electrodes and electrical contact members.

13. A method for determining absolute positions of a first device member relative to a second device member of a medication delivery device, the method comprising:
   providing a plurality of electrically conducting electrodes forming a first group of electrodes and a second group of electrodes arranged on the outer surface part of said first device member of the medication delivery device, wherein the plurality of electrically conducting electrodes of the first and second group of electrodes are electrically interconnected through respective electronic devices each having a measurable electronic value;
   providing first and second contact members and third and fourth contact members arranged on the second device member of the medication delivery device, the first and second contact members and third and fourth contact members being adapted to establish galvanic electrical connections to respective ones of electrically conducting electrodes of the first and second group of electrodes, respectively, said first and second contact members and said third and fourth contact members further being adapted to be slid across the first group of electrodes when the first device member is moved relative to the second device member so that the first and second contact members and third and fourth contact members galvanically connect to respective ones of said electronic devices as the first device member is moved relative to the second device member;
   determining the measurable electronic value of respective electronic devices between the first and second contact members and the third and fourth contact members, wherein said determining relies on measuring the resistance between the four individual contact members, and comparing the determined measurable electronic value with a set of predetermined values to uniquely identify the position of the first device member relative to the second device member; and
   thereby determining absolute positions of the first device member relative to the second device member of a medication delivery device.

14. A method according to claim 13, wherein the determining of the measurable electronic value, and the comparison of the determined measurable electronic value with a set of predetermined values is performed by an electronic control circuit integrated in the medication delivery device.

15. A method according to claim 13, further comprising determining additional measurable electronic values of respective ones of additional electronic devices connecting additional electrically conducing electrodes of the first group, and comparing the determined additional measurable electronic values with the set of predetermined values.

16. A method according to claims 13, comparing the determined resistance with a set of predetermined values.

17. A method according to claim 13, wherein the predetermined values are arranged in a look-up table.

18. A method according to claim 13, wherein the first device member is adapted to perform a translational movement relative to the second device member.

19. A method according to claim 13, wherein the first device member is adapted to perform a rotational movement relative to the second device member.

20. A method according to claim 13, wherein the first device member is adapted to perform a combined rotational and translational movement relative to the second device member.

21. A method according to claim 13, wherein the contact members are mechanically biased towards the first device member.

22. A method according to claim 13, wherein the contact members are arranged in a fixed relationship with the second device member.

23. A method according to claim 13, wherein the first device member forms part of a rotatably mounted dose indicator barrel.

24. A method according to claim 13, wherein the second device member forms part of a housing of the medication delivery device.

25. The method according to claim 13, further comprising additional pairs of electrodes and electrical contact members.

* * * * *